United States Patent [19]

Mirowski et al.

[11] Patent Number: 4,572,191
[45] Date of Patent: Feb. 25, 1986

[54] COMMAND ATRIAL CARDIOVERTER

[75] Inventors: Mieczyslaw Mirowski, Rte. 3, Velvet Valley Way, Owings Mills, Md. 21117; Morton M. Mower, Baltimore, Md.; Alois A. Langer, Pittsburgh, Pa.

[73] Assignee: Mieczyslaw Mirowski, Owings Mills, Md.

[21] Appl. No.: 581,229

[22] Filed: Feb. 23, 1984

Related U.S. Application Data

[63] Continuation of Ser. No. 349,473, Feb. 17, 1982, abandoned, which is a continuation of Ser. No. 65,228, Aug. 9, 1979, Pat. No. 4,316,472, which is a continuation of Ser. No. 641,381, Dec. 17, 1975, abandoned, which is a continuation of Ser. No. 464,180, Apr. 25, 1974, Pat. No. 3,952,750.

[51] Int. Cl.$^4$ ............................................. A61N 1/36
[52] U.S. Cl. ................................................ 128/419 D
[58] Field of Search .................................... 128/419 D

[56] References Cited

U.S. PATENT DOCUMENTS

| | | | |
|---|---|---|---|
| 3,195,540 | 7/1965 | Waller | 128/419 PG |
| 3,241,556 | 3/1966 | Zacouto | 128/419 PG |
| 3,311,111 | 3/1967 | Bowers | 128/419 PG |
| 3,442,269 | 5/1969 | Druz | 128/419 D |
| 3,513,850 | 5/1970 | Weber | 128/419 D |
| 3,614,954 | 10/1971 | Mirowski et al. | 128/419 D |
| 3,738,370 | 6/1973 | Charms et al. | 128/419 D |
| 3,747,605 | 7/1973 | Cook | 128/419 D |
| 3,805,795 | 4/1974 | Denniston et al. | 128/419 D |
| 3,805,796 | 4/1974 | Terry, Jr. et al. | 128/419 PG |

*Primary Examiner*—William E. Kamm
*Attorney, Agent, or Firm*—Fleit, Jacobson, Cohn & Price

[57] ABSTRACT

An externally controlled implantable electronic device for delivering a cardioverting pulse of energy to an ailing heart. A defibrillator produces a first signal when its storage device is fully charged and ready to be discharged, and a second signal when a predetermined characteristic of an ECG signal is detected. An actuator is provided for determining the presence of both of these signals. If during a predetermined time period, there is a simultaneous occurrence of the first and second signals, then the defibrillator will be activated to deliver the cardioverting shock to the heart. In the absence of either of the two signals, the defibrillator will not deliver a shock.

14 Claims, 3 Drawing Figures

COMMAND ATRIAL CARDIOVERTER

This application is a continuation of application Ser. No. 349,473, filed Feb. 17, 1982, now abandoned, which is a continuation of Ser. No. 065,228, filed Aug. 9, 1979, now U.S. Pat. No. 4,316,472, which is a continuation of Ser. No. 641,381, filed Dec. 17, 1975, now abandoned, which is a continuation of Ser. No. 464,180, filed Apr. 25, 1974, now U.S. Pat. No. 3,952,750.

BACKGROUND OF THE INVENTION

There are scores of individuals walking the streets today who experience recurring episodes of atrial fibrillation, atrial flutter, or tachycardia. While not life-threatening, these supra-ventricular arrhythmias can become debilitating and lead to complications, and hence require treatment when present. Such individuals require frequent electrical or pharmacological conversion under the care of their physicians to return their heats to normal sinus rhythm.

Drug therapy is not infrequently successful in correcting atrial fibrillation, flutter or tachycardia, but there are many patients who are resistant to the appropriate drugs or who suffer serious side-effects from the drugs. For these patients, cardioversion is accomplished by way of a technique in which a pulse generator and external paddles combine to send high energy electrical pulses through the ailing patient's thorax to the heart.

For those who suffer from recurring bouts of atrial tachyarrythmias, regular and often times frequent visits to hospitals are in order. Those whose hearts can be successfully returned to normal sinus rhythm by way of drug therapy frequently undergo hospitalization so that the effects of the administered drugs can be carefully monitored. Similarly, those requiring electrical cardioversion are generally cardioverted in the hospital due to the fact that the procedure frequently requires the application of a general anesthetic and carries with it a significant risk to the patient.

It is toward the facilitation of treatment for and the reduction of the risks to those patients suffering from recurring episodes of atrial fibrillation, flutter and tachycardia, that the present invention is directed.

SUMMARY OF THE INVENTION

The present invention relates to an atrial device designed to be implanted under the skin of patients who frequently suffer from bouts of atrial fibrillation, flutter or tachycardia. During those times when the patient is suffering such an arrhythmia, and cardioversion is in order, a command given by the patient or his physician brings the inventive device out of its standby condition to administer a low-level pulse of energy directly to the heart, for example, through a catheter implanted in or about the atrium. Cardioversion by means of an electrical discharge delivered through an intra-atrial catheter has been shown to require energies of five watt-seconds or less, and is thus a painless procedure not requiring anesthesia.

In one embodiment of the present invention, the patient will likely visit the office of his physician for treatment. By way of an external console, the physician programs the desired level of cardioverting energy to be administered. Then, both the power to charge an implanted discharge capacitor and a set of control signals corresponding to the programmed level of cardioverting energy is transmitted through the skin of the patient and into the implanted unit. In addition, the invention contemplates that an ECG synchronization signal be derived either internally or from an external ECG unit and fed back through the skin of the patient as a command signal to ensure that cardioversion occurs in proper synchronization with the QRS complex. With the present invention, provision can be made to discharge the stored energy through a test load for verifying the readiness of the implanted unit, and information can be extracted through the skin of the patient so that the physician is able to monitor the discharge of the implanted capacitor, which is either through the test load or the implanted atrial catheter.

In another embodiment of the present invention, the patient is able to cardiovert himself at home, without the intervention of his physician. The patient who frequently undergoes attacks of atrial fibrillation, flutter or tachycardia can be taught to recognize the symptoms of such arrhythmias. Once able to recognize that he or she is experiencing such an attack of a convertible arrhythmia, the patient can effect cardioversion when appropriate.

In the second patient-operated embodiment of the present invention, an energy source is incorporated into the implanted cardioverting device. The energy source is normally maintained out of the cardioverting circuit, and is connected into the circuit only upon the issuance of an appropriate command. As here disclosed, the patient issues this command by holding a magnet at an appropriate location against his skin, and a reed switch closes. Upon the closing of the reed switch, the energy source is brought into the circuit, and the discharge cycle is initiated.

In the embodiment of the present invention designed for operation by a physician, the level of cardioverting energy to be delivered to the patient can be manually programmed. In the embodiment of the invention designed for operation without the intervention of a physician, it is also possible to deliver the cardioverting shocks in varied energy levels. In this regard, the patient-operated embodiment of the invention comtemplates sequentially increasing the cardioverting energy level over prior attempts at cardioversion. Specifically, the first attempted cardioversion can be at a relatively low energy level. Then, if unsuccessful, a higher energy can be applied, and so forth. As disclosed, the patient controls repeated discharges by way of the duration of magnet placement against his skin. If low-energy cardioversion is attained, the patient merely removes the magnet from the location of the reed switch. If cardioversion is unsuccessful, the magnet is maintained in position, and the implanted circuitry automatically increases the energy level for the next attempted cardioversion.

Like the first, the second embodiment of the present invention can be equipped with circuitry for synchronizing the cardioverting shocks with the QRS complex. This can be accomplished by way of a sensing probe positioned in or about the heart.

Accordingly, it is one object of the present invention to provide a device which will enable the cardioversion of a heart undergoing atrial fibrillation, flutter or tachycardia, without hospitalization.

Another object of the present invention is to provide a device which will so cardiovert an ailing heart, comfortably and without the administration of an anesthetic.

Additional objects of the present invention are to provide an implanted device whose operation is capable of being verified before discharge into the heart, whose discharge is capable of being synchronized with the QRS complex, in which the energy level of the discharge can be manually programmed or automatically increased in successive attempts at cardioversion, and whose discharges can be monitored from external to the skin of the patient.

Yet another object of the present invention is to provide a method for cardioverting a heart suffering from an atrial malfunctioning, wherein cardioversion is initiated by a physician or by the wearer while in a state of consciousness, and wherein cardioversion is accomplished by an implanted electronic device manually triggered from external to the skin of the wearer.

These and other objects of the present invention, as well as many of the attendant advantages thereof, will become more readily apparent when reference is made to the following description taken in conjunction with the accompanying drawings.

DETAILED DESCRIPTION OF THE DRAWINGS

Figure 1:
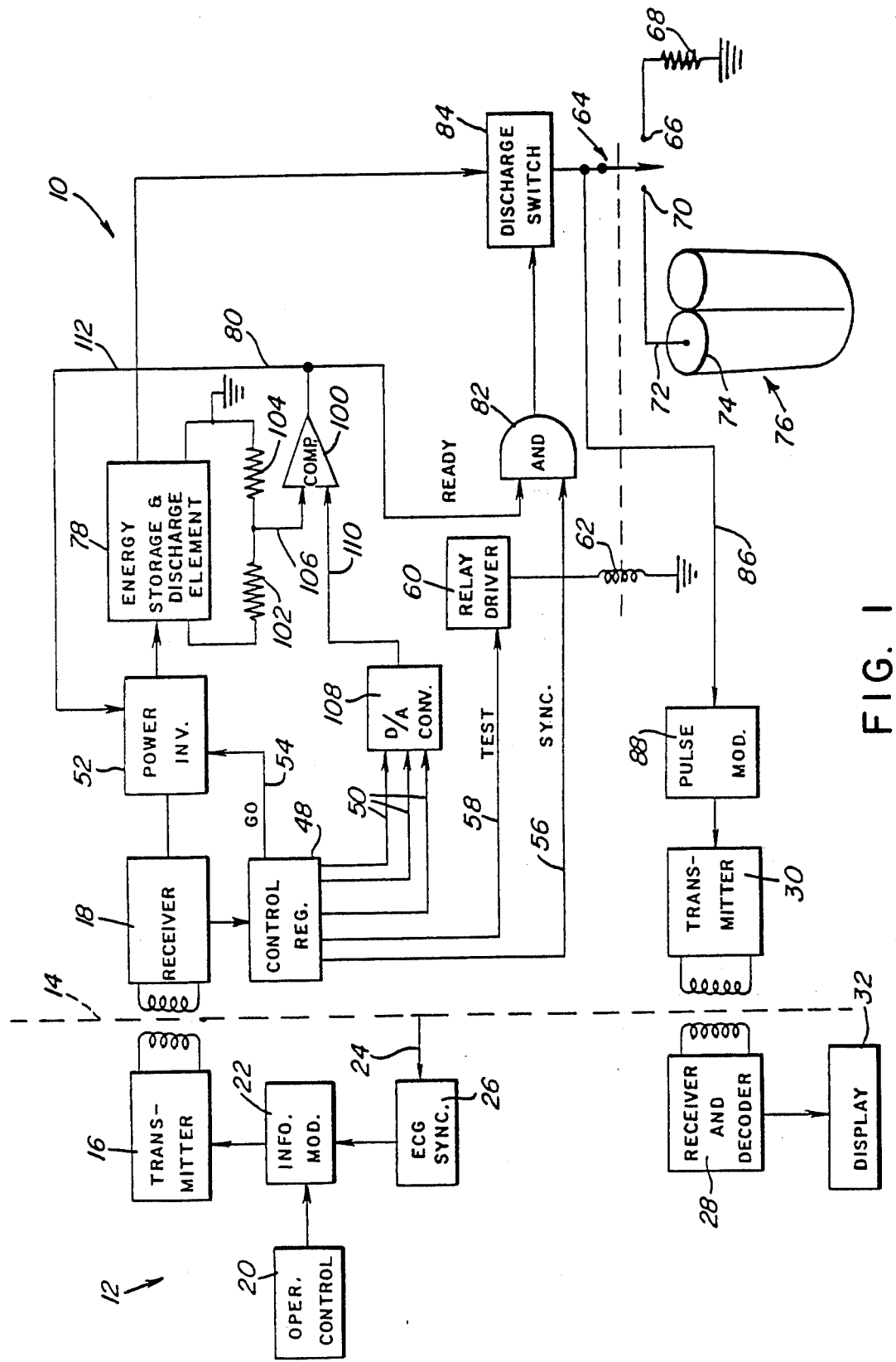
FIG. 1 is a block diagram of an embodiment of the inventive implantable command device particularly suited for use in the office of a physician.
Figure 2:
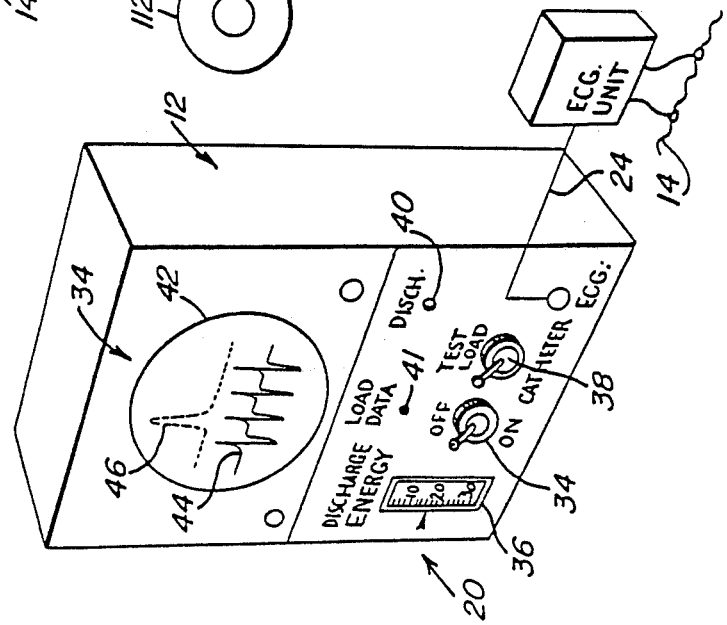

With reference initially to FIGS. 1 and 2, the first embodiment of the present invention will be described. The inventive implantable command device is indicated generally at 10 and is adapted to associate with an external console generally designated at 12. Console 12 includes circuitry for transmitting power and control information to the implanted device for receiving information about the nature of the cardioverting pulses from the implanted device as well as signals from other cardiac equipment, and for visually displaying selected cardiac information. The numeral 14 schematically represents the skin of the patient, and hence shows the separation between the implanted device 10 and the external console 12.

The console 12 comprises a power and information transmitter 16 which communicates with an implanted receiver unit 18. Information such as the desired cardioverting energy, whether the unit should be in its "test" or its operating mode, etc., all of which will be explained below, is programmed into an operating control unit 20. Unit 20 may, for example, include a plurality of on-off switches which generate digital signals. The digital signals from operating control unit 20 are fed in parallel to an information modulator circuit 22 where they are converted into a serial chain of operating commands.

Schematically illustrated in FIG. 1 at 24 is an ECG input which may be in the form of a conventional ECG unit or an amplifier which is made an integral part of the console 12. A sequence of electrocardiograph signals taken from the skin 14 of the patient is further illustrated at 44 in FIG. 2. From the electrocardiograph input 24 can be derived impulses which are representive of the occurrence of the QRS complex. The QRS impulses are fed to the information modulator 22 as is schematically represented, from the ECG synchronization unit 26.

Also part of the external console 12 is a receiver and decoder 28 which is adapted to receive and decode information transmitted by the implanted transmitter 30. After being decoded, the information delivered across the skin 14 by transmitter 30 is displayed at an external display unit 32. As can be seen, the implanted transmitter 30 sends signals across the skin 14 of the patient to the receiver and decoder 28 much the same as external transmitter 16 sends signals to implanted receiver 18. Of course, the particular form of modulation could be different.

As represented in FIG. 1, power and information signals are transmitted through the skin of the patient by way of coupled transformer primary and secondary windings. In the specific physician-controlled embodiment herein illustrated and described, power to the implanted unit and the control information is, for simplicity, transmitted along the same channel. The control information can be modulated into the power channel by frequency shift keying, pulse width modulation, or any other appropriate well-known modulation technique.

With specific reference to FIG. 2, the external console 12 can be seen to include a display portion 32 and an operating control panel generally designated at 20. Control panel 20 is equipped with an on/off switch 34, an input for the ECG signals 24, a rotary energy discharge dial 36 to enable the physician to control the amount of energy discharged into the heart, a toggle switch 38 for controlling whether the stored energy is discharged into a test load or into the heart, a push button 40 to initiate the discharge of the implanted storage capacitor, and a load-data push button 41. Also illustrated as part of the display portion of external console 12 is a cathode ray tube 42 shown as simultaneously displaying the periodic QRS complex 44 and, in broken lines, the discharge of the implanted storage capacitor.

With continuing reference to FIGS. 1 and 2, the operation of the external unit will be described. The patient suffering from a convertable atrial arrythmia, such as atrial fibrillation, flutter or tachycardia, is examined by the physician, preferably with the aid of ECG equipment. Based upon this input, the physician makes his best estimate of the energy level which will be required to cardiovert the malfunctioning heart, and sets rotary dial 36 accordingly. The ECG synchronization input is then connected to the console 12, the toggle switch 38 is set to either the test load or catheter discharge position, and toggle 34 is moved to the "on" position. At this time, the unit is functional, with energy being transmitted to the implanted circuitry, and with ECG signals being displayed on the display device 32 as shown at 44. The physician then presses the load-data button 41 to transmit the instructions regarding the level of the discharge pulse to the implanted unit at which time the energy storage capacitor is charged to the desired level. When ready, the "discharge" button 40 is depressed, and either the test load or the heart is shocked at the proper time during the QRS complex. The test load is, of course, intended to verify attaining the proper level of discharge before a shock is actually applied to the heart. When the discharge level is verified, the physician simply moves switch 38 to the catheter position, presses the load-data button and then the "discharge" button 40 to deliver a pulse to the heart.

Once a shock is actually applied to the heart, the physician observes the screen of CRT 42, and either concludes his activity if cardioversion is successful, or repeats the cardioverting attempt at perhaps a higher energy level if unsuccessful.

When the rotary energy dial 38 and the other controls on panel 20 are set by the physician, the operating control unit 20 provides, for example, a binary signal representative of the energy level to which the dial 36 is set and other operating parameters. This signal takes the form of a parallel binary control word. As noted above, the rotary dial 36 could be replaced by a set of toggle switches, each one of which would provide a discrete binary control signal. The parallel binary control word from the operating control unit 20, as illustrated in FIG. 1, is delivered to the information modulator 22 where it is converted into a serial binary control word. From modulator 22, the serial control word is delivered to the transmitter 16 and sent to the implanted device along the information channel. Simultaneously, the ECG synchronization signal is delivered to the modulator 22.

When the on/off switch 34 on the external console 12 is in the "on" position, the transmitter 16 is activated, and energy in the form of power signals is transformer coupled across the skin of the patient. This energy is received through the secondary winding of the coupling transformer at receiver 18. Then, when the load-data button 41 is depressed, the serial binary control word is transmitted along the information channel. The serial control word recovered by the receiver 18 takes the form of a timed set of pulses. The receiver 18 directs these serial pulses to a control register 48 which reconstructs them into their original parallel format. The parallel control word, along with other control information, provides a signal proportional to the desired energy level which is then transmitted via discrete lines 50 to circuitry associated with a power inverter 52.

Before the activity of the power inverter 52 is initiated, the control register 48 issues a "go" signal which confirms receipt of the control word from the receiver 18. This may be accomplished in any of several well-known ways, for example, by ending each control word with a unique character to designate its end. This "go" command is indicated at 54. As represented in FIG. 1, with three energy control lines 50, a maximum of eight power levels can be set, as a binary format is used. The specific operation of the power inverter 52 and the associated circuitry which serves the purpose of charging the storage capacitor at a predetermined energy level, will be explained below.

The receiver 18 also feeds to the control register 48, information related to the QRS synchronization and whether the energy storage device is to be discharged into the implanted catheter or into a test load. As seen in FIG. 1, the synchronization signal is carried along lead 56 while the test-mode signal is directed along lead 58. The signal on line 58 is fed to a relay driver 60 which associates with coil 62 and in turn, a switch 64. In one position of the switch 64, indicated at 66, energy is directed into a test load 68. In the other position, designated 70, the discharge capacitor feeds directly to a catheter 72 implanted in or about the atrium 74 of a heart 76.

When activated, the power inverter 52 directs energy to an energy storage and discharge device 78 which in this case takes the form of a storage capacitor. When the energy stored by the capacitor 78 reaches the level set on the rotary dial 36, as will be fully explained below, a "ready" signal is produced by a comparator 100 and fed via line 80 to an AND gate 82. The same "ready" signal is also fed back to the power inverter 52.

The "ready" signal which is produced by the comparator 100 is indicative of the discharge capacitor being in readiness for firing through a discharge switch 84. Synchronization signals are, at this time, fed to the AND gate 82 along with the "ready" signal on line 80, and upon the simultaneous occurrence of a "ready" signal on line 80 and a QRS synchronization pulse on line 56, AND gate 82 responds by issuing a signal which controls the state of switch 84, and firing the capacitor 78 through the discharge switch. The position of switch 64 determines whether the capacitor 78 fires through the test load 68 or through the catheter 72.

The capacitor 78 is charged as explained below. When the control register 48 produces the "go" signal at line 54, this signal reaches a gate input of the power inverter 52. Power inverter 52 can be on any conventional inverter design which produces an output somewhere on the order of 600 volts and can be gated "on" and "off" by the application of external gating commands. The "go" signal from the control register 48 gates the power inverter 52 on, and the relatively constant 600 volt output is thereby initiated. The output of the power inverter 52 is fed directly to the capacitor 78.

As can be seen, a resistive divider in the form of a pair of resistors 102 and 104 is connected across capacitor 78, and the signal appearing at the junction between the resistors 102 and 104 is tapped into one input terminal 106 of comparator 100. The "energy control" command which is produced at the control register 48 and fed along lines 50 forms the input to a digital-to-analog converter 108. The converter 108 is of conventional design, with its analog output being directed to the other input terminal 110 of comparator 100.

When the voltage across capacitor 78 reaches the present desired level, the signal reaching the input 106 of comparator 100 balances the control signal at input 110. At this time, the comparator 100 produces a "ready" signal which is simultaneously transmitted to AND gate 82 along line 80 and to power inverter 52 along feedback path 112. The "ready" signal on line 112 gates the power inverter 52 into its off state. At this point in time, the capacitor 78 is fully charged and in readiness for discharging into either the test load or the heart, and hence the charging operation is completed.

As noted previously, the present invention comtemplates an implanted transmitter 30 associated with the receiver and decoder 28 forming a part of the external console 12. The discharge of the capacitor 78 through either the test load 68 or the catheter 72 is monitored at line 86 which directs a pulse representative of the discharge to a pulse modulator 88. The pulse modulator feeds a modulated signal to transmitter 30 which, in turn, transformer couples the signal across the skin 14 of the patient and to the external receiver and decoder 28. After decoding, the signal representative of the delivery of an electrical shock is displayed on the CRT as at 46 in FIG. 2.

Now, with reference to FIG. 3, the totally inplantable embodiment of the inventive elective atrial device will be described. For convenience of description, those elements which have previously been described with reference to FIG. 1 are similarly numbered in FIG. 3, and will not again be described in detail.

Figure 3:
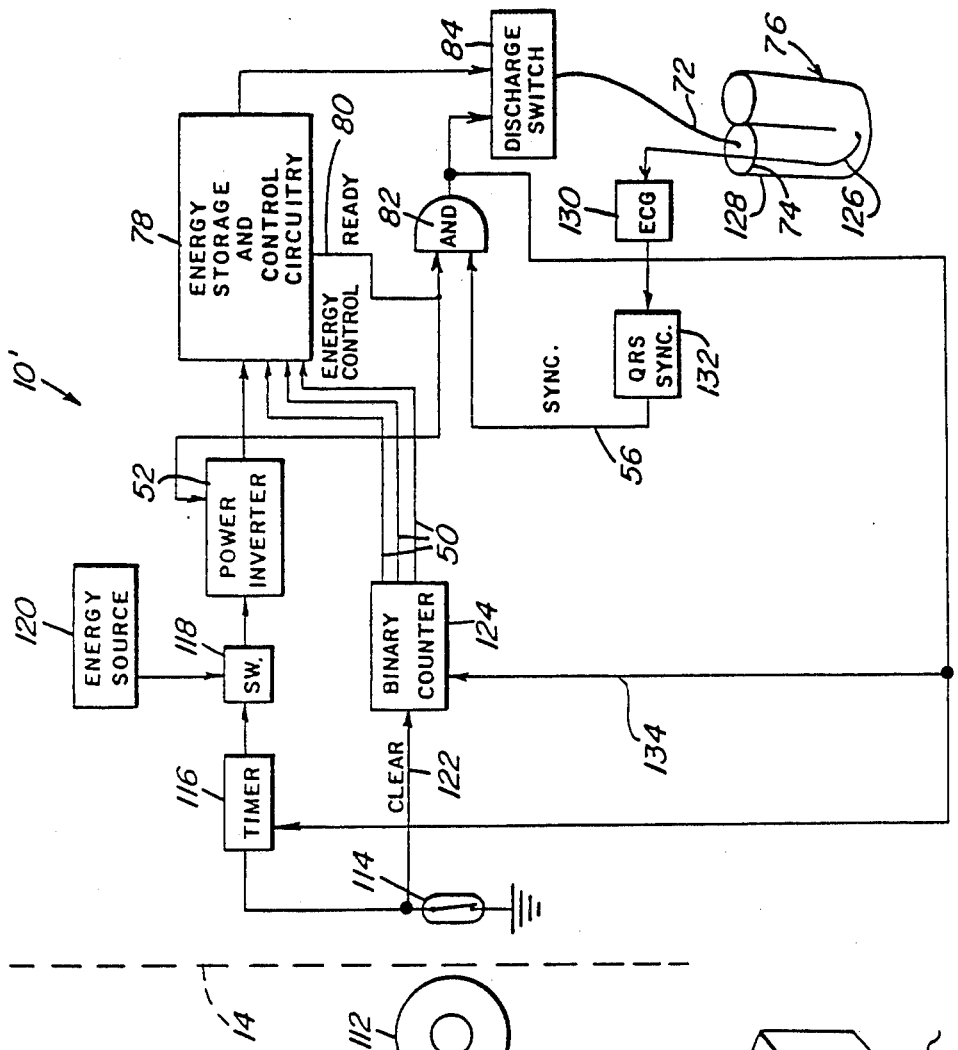
FIG. 2 pictorially depicts the physician's console which is represented in FIG. 1 as associating with the inventive implantable device and FIG. 3 is a block diagram of another embodiment of the inventive implantable command device suitable for operation without the intervention of a physician.

In the embodiment illustrated in FIG. 3, each element of the inventive device is implanted beneath the skin 14 of the patient with the exception of a command magnet 112. Here, the patient controls the operation of the implanted device by positioning the command magnet 112 at a location on his body immediately opposite an implanted reed switch 114. When so positioned, reed switch 114 closes, and the implanted device is actuated.

The fully implanted device is generally shown in FIG. 3 at 10'. After the reed switch 114 closes, a timer 116 is turned on and, after a preset delay set into the timer, a switch 118 is closed to direct energy from an implanted battery 120 to the input of the power inverter 52. Simultaneous with the closing of the reed switch 114, a "clear" signal is issued along line 122 and is fed to a binary counter 124 to reset the same to its initial state. It should of course be appreciated that closure of the reed switch 114 also delivers operating power to the timer 116 and to the binary counter 124, but such connections have been eliminated to simplify the block diagram of FIG. 3.

As is evident from FIG. 3, an ECG signal is derived by way of a catheter 126 implanted in or about the heart, as in the right ventricle 128. This ECG signal is further developed at ECG circuitry 130, and synchronization pulses are in turn produced at a QRS synchronization circuit 132. As before, the "ready" signal from the inverter-capacitor circuit and the synchronization signal from the QRS synchronization circuit 132 are both fed to an AND gate 82. Upon coincidence of the "ready" and synchronization signals, AND gate 82 switches the discharge switch 84 to its conductive state, thereby discharging the storage and discharge capacitor 78 through the heart 76 by way of a catheter 72 implanted in or about the heart, as in the right atrium 74.

The operation of the circuit illustrated in FIG. 3 is as follows. When the knowledgeable patient experiences either atrial fibrillation, flutter or tachycardia, and elects to undergo cardioversion, he places the command magnet 112 at the appropriate location near the reed switch 114. The magnetic pull closes the reed switch 114, clears the binary counter 124, and places the timer 116 in its counting state. After a preset delay, timer 116 produces a command which places switch 118 in its conductive state, and hence energy is delivered from the source 120 to the power inverter 52.

Once being cleared, binary counter 124 takes its first state which commands power inverter 52 to charge the discharge capacitor 78 to its lowest predetermined energy level. This is accomplished by the binary counter 124 developing an energy control signal, and feeding the same to the power inverter 52 along lines 50. In the same manner as explained above, when discharge capacitor 78 reaches the proper level of charging, a "ready" signal is issued and is passed to AND gate 82 via line 80. At the same time, the ventricular catheter 126 or another appropriate sensing lead senses the heart function, and a set of QRS synchronization pulses is produced by circuit 132 and fed to AND gate 82 via line 56.

Upon the simultaneous occurrence of a "ready" signal and a QRS pulse, AND gate 82 switches discharge switch 84 to its conductive state and the discharge capacitor 78 discharges through the heart 76 of the patient via atrial catheter 72. Firing of capacitor 78 through the atrial catheter 72 issues a signal at line 134 which sets binary counter 124 to its second state. At the same time, the delay period of timer 116 is reinitiated to enable the patient to assess the effect of the first pulse.

If the patient successfully undergoes cardioversion, the command magnet 112 is removed, and the procedure is completed. If, however, after the elapse of the time delay set in timer 116, the patient determines that his heart is still in fibrillation, or undergoing flutter or tachycardia, another cardioversion will be attempted. With the inventive circuit, this second attempt is at a higher energy level.

After deciding that a second attempt at cardioversion is appropriate, the patient maintains command magnet 112 in its position opposite reed switch 114. As such, there is no "clear" signal issued to binary counter 124, and counter 124 remains in its second state after being advanced by the first discharge of the capacitor 78 through the heart. The preset delay in timer 116 elapses, and switch 118 is placed in its conductive state. Therefore, energy source 120 again energizes power inverter 52. Binary counter 124, then being in its second state, commands power inverter 52 to charge energy storage and discharge capacitor 78 to a higher level of energy. When capacitor 78 reaches this higher energy level, the capacitor is again dischared through the heart in proper synchronization with the QRS complex. This stepped discharge through the heart can be programmed, as desired, by presetting the number of stages of the binary counter 124.

It should be appreciated that as shown in the embodiment illustrated in FIG. 3, the QRS synchronization signal can be taken internally, as, for example, from a catheter implanted in the ventricle. Such an arrangement can also be used in the device of FIG. 1 in lieu of the external ECG console. Furthermore, while the specific embodiment of FIG. 3 employs a multi-stage discharge in increasing energy levels, such is not necessary in the basic design of the implantable device. Rather, the binary counter and associated circuitry can be eliminated, and the power inverter 52 set so that the first discharge through the heart is at a level sufficient to cardiovert the heart under most conditions of fibrillation, flutter and tachycardia. Furthermore, while synchronization with the QRS complex is believed to increase the safety factor involved in cardioverting a malfunctioning heart, cardioversion can be accomplished without synchronization. Under these conditions, the internal ventricular catheter and QRS circuitry could be eliminated.

While specific embodiments of the present invention have been described, it should be understood that these embodiments are described for purposes of illustration only. The foregoing description is not intended in any way to limit the scope of the present invention. Rather it is the intention that the scope of the invention be limited only as defined in the appended claims.

What is claimed is:

1. A cardioverting device comprising:
   detecting means for issuing an electrical signal representing the actual ECG activity of the heart of a wearer of the device;
   storage means for storing energy to convert an abnormal cardiac rhythm to normal sinus rhythm;
   delivery electrode means for discharging the stored energy into the heart of the wearer;
   switch means for controlling the discharge of the stored energy into the heart of the wearer;
   charging means for delivering to said storage means said energy to convert the abnormal cardiac rhythm;

first monitoring means for monitoring the operation of said storage means and issuing a first signal when said storage means has stored a predetermined amount of energy;

second monitoring means for monitoring the ECG signal produced by said detecting means and for detecting a preselected repeatable characteristic of the ECG signal, said monitoring means further including means for issuing a second signal each time said second monitoring means detects said preselected repeatable characteristic of the ECG signal;

third monitoring means for monitoring the ECG signal produced by said detecting means for activating said charging means in the presence of abnormal cardiac rhythm in need of correction; and actuating means connected to said first and second monitoring means and requiring the simultaneous presence of said first and second signals at the time the stored energy is to be delivered to the heart of the wearer, said actuating means for actuating said switching means.

2. The cardioverting device of claim 1, and further comprising counter means made operative upon the activation of said cardioverting device for producing a count signal when a predetermined count is reached; means responsive to said count signal for increasing the amount of energy stored by said storage means for successive discharges of the stored energy into the heart of the wearer.

3. The cardioverter of claim 2 wherein said counter means is a multi-stage device for producing command signals determinative of the amount of energy which said charging means delivers to said storage means; and wherein said charging means includes means for progressively increasing the amount of energy delivered to said storage means in successive stages of said counter means.

4. The cardioverter of claim 2, wherein said counter means includes means for advancing said counter means a predetermined amount for each discharge of said stored energy into the heart.

5. The cardioverter of claim 4, further comprising means external to the skin of the wearer for activating said switch means, and wherein said counter means includes means for returning said counter means to its initial stage before each operation of said switch means.

6. The cardioverting device of claim 2, wherein the portion of said heart receiving said discharges of said stored energy is the atrium.

7. The cardioverting device of claim 1, further comprising selecting means for selecting a predetermined magnitude from among a plurality of selectable magnitudes of energy stored in said charging means.

8. The cardioverting device of claim 7, wherein said selecting means includes means external to the body of the wearer for permitting manual selection of the predetermined magnitude.

9. The cardioverting device of claim 7, wherein said selecting means includes means for initially selecting a relatively low energy for delivery to said storage means, and responding to each attempt to convert an abnormal cardiac rhythm to normal sinus rhythm by an incremental increase in the energy to be delivered to said storage means.

10. The cardioverting device of claim 1, wherein said detecting means includes means external to the body of the wearer for detecting said ECG signal.

11. The cardioverting device of claim 1, wherein said detecting means includes means implanted in the body of the wearer for detecting said ECG signal.

12. The cardioverting device of claim 1, wherein said preselected characteristic of the ECG signal is the QRS complex.

13. The cardioverting device of claim 1, further comprising means for deactivating said charging means upon the issuance of said first signal by said first monitoring means.

14. The cardioverting device of claim 1, wherein said charging means includes a source of energy external to the body of the wearer, and means for transmitting the energy through the skin of the wearer to said storage means which is implanted in the wearer.

* * * * *

REEXAMINATION CERTIFICATE (4184th)

United States Patent [19]
Mirowski et al.

[11] B1 4,572,191
[45] Certificate Issued Oct. 24, 2000

[54] COMMAND ATRIAL CARDIOVERTER

[75] Inventors: Mieczyslaw Mirowski, Rte. 3, Velvet Valley Way, Owings Mills, Md. 21117; Morton M. Mower, Baltimore, Md.; Alois A. Langer, Pittsburgh, Pa.

[73] Assignee: Mieczyslaw Mirowski, Ownings Mills, Md.

Reexamination Request:
No. 90/005,126, Oct. 26, 1998

Reexamination Certificate for:
Patent No.: 4,572,191
Issued: Feb. 25, 1986
Appl. No.: 06/581,229
Filed: Feb. 23, 1984

Related U.S. Application Data

[63] Continuation of application No. 06/349,473, Feb. 17, 1982, abandoned, which is a continuation of application No. 06/065,228, Aug. 9, 1979, Pat. No. 4,316,472, which is a continuation of application No. 05/641,381, Dec. 17, 1975, abandoned, which is a continuation of application No. 05/464,180, Apr. 25, 1974, Pat. No. 3,952,750.

[51] Int. Cl.[7] ............................................. A61N 1/36
[52] U.S. Cl. .................................... 607/7; 607/61
[58] Field of Search ................................................ 607/5

[56] References Cited

U.S. PATENT DOCUMENTS

| | | | |
|---|---|---|---|
| Re. 27,652 | 5/1973 | Mirowski et al. | 128/419 D |
| Re. 30,372 | 8/1980 | Mirowski et al. | 128/49 D |
| Re. 30,387 | 8/1980 | Denniston, III et al. | 128/419 D |
| Re. 30,750 | 9/1981 | Diack et al. | 128/419 D |
| 3,144,019 | 8/1964 | Haber | 128/2.06 |
| 3,236,239 | 2/1966 | Berkovits | 128/419 |
| 3,241,555 | 3/1966 | Caywood et al. | 128/421 |
| 3,253,596 | 5/1966 | Keller, Jr. | 128/421 |
| 3,258,013 | 6/1966 | Druz | 128/419 |
| 3,389,704 | 6/1968 | Buchowski et al. | 128/419 |
| 3,431,912 | 3/1969 | Keller, Jr. | 128/422 |
| 3,527,228 | 9/1970 | McLaughlin | 128/419 |
| 3,527,229 | 9/1970 | Kempen | 128/419 |
| 3,528,428 | 9/1970 | Berkovits | 128/421 |
| 3,605,754 | 9/1971 | Jaros et al. | 128/419 D |

(List continued on next page.)

FOREIGN PATENT DOCUMENTS

| | | |
|---|---|---|
| 240961 | 9/1972 | Argentina . |
| 0 023 134 A1 | 1/1981 | European Pat. Off. . |
| 2 130 295 | 11/1972 | France . |
| 22 12 591C2 | 10/1972 | Germany . |
| 171 326 | 10/1982 | Netherlands . |
| 389022 | 9/1972 | Sweden . |
| 1 356 190 | 6/1974 | United Kingdom . |
| 1 416 197 | 12/1975 | United Kingdom . |
| 1 502 331 | 3/1978 | United Kingdom . |
| 2 002 156 | 2/1979 | United Kingdom . |
| 2 036 870 | 2/1980 | United Kingdom . |

OTHER PUBLICATIONS

B. Lown et al., "New Method for Terminating Cardiac Arrhythmias: Use of Synchronized Capacitor Discharge," Journal of the American Medical Association, vol. 182, No. 5, (Nov. 3, 1962) pp. 150–157.

M. Mirowski et al., "Miniaturized Implantable Automatic Defibrillator for Prevention of Sudden Death From Ventricular Fibrillation," Proceedings of the Vth International Symposium on Cardiac Pacing, (Mar. 14–18, 1976) pp. 103–106.

*Primary Examiner*—William E. Kamm

[57] ABSTRACT

An externally controlled implantable electronic device for delivering a cardioverting pulse of energy to an ailing heart. A defibrillator produces a first signal when its storage device is fully charged and ready to be discharged, and a second signal when a predetermined characteristic of an ECG signal is detected. An actuator is provided for determining the presence of both of these signals. If during a predetermined time period, there is a simultaneous occurrence of the first and second signals, then the defibrillator will be activated to deliver the cardioverting shock to the heart. In the absence of either of the two signals, the defibrillator will not deliver a shock.

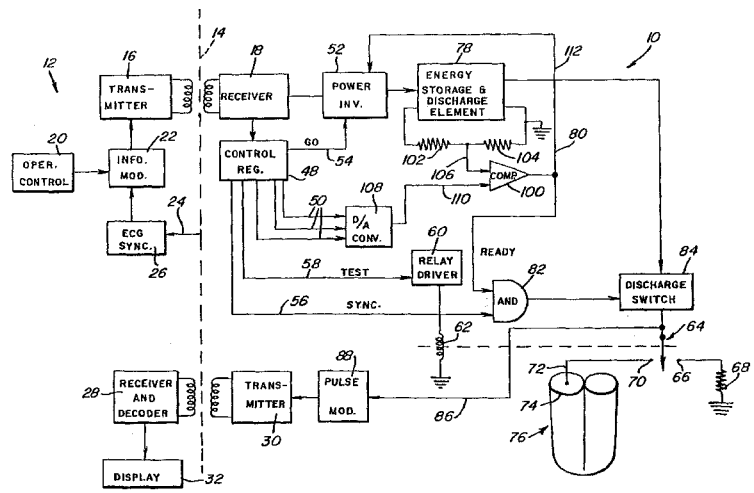

U.S. PATENT DOCUMENTS

| Patent # | Date | Inventor | Class |
|---|---|---|---|
| 3,614,955 | 10/1971 | Mirowski et al. | 128/419 D |
| 3,631,860 | 1/1972 | Lopin | 128/419 P |
| 3,662,758 | 5/1972 | Glover | 128/419 E |
| 3,693,627 | 9/1972 | Berkovits | 128/419 P |
| 3,698,386 | 10/1972 | Fried | 128/2.06 A |
| 3,703,900 | 11/1972 | Holznagel | 128/419 P |
| 3,716,059 | 2/1973 | Welborn et al. | 128/419 D |
| 3,717,140 | 2/1973 | Greenwood | 128/2.05 T |
| 3,717,153 | 2/1973 | Bowers | 128/419 P |
| 3,718,909 | 2/1973 | Greatbatch | 340/167 A |
| 3,724,455 | 4/1973 | Unger | 128/2.06 A |
| 3,726,285 | 4/1973 | Bowers et al. | 128/419 P |
| 3,727,616 | 4/1973 | Lenzkes | 128/422 |
| 3,747,605 | 7/1973 | Cook | 128/419 D |
| 3,782,389 | 1/1974 | Bell | 128/419 D |
| 3,798,542 | 3/1974 | Dempsey | 324/133 |
| 3,832,994 | 9/1974 | Bicher et al. | 128/2.06 A |
| 3,833,005 | 9/1974 | Wingrove | 128/419 P |
| 3,857,398 | 12/1974 | Rubin | 128/419 D |
| 3,860,009 | 1/1975 | Bell et al. | 128/419 D |
| 3,862,636 | 1/1975 | Bell et al. | 128/419 D |
| 3,870,050 | 3/1975 | Greatbatch | 128/419 PG |
| 3,881,467 | 5/1975 | Stanly et al. | 128/2.06 A |
| 3,886,950 | 6/1975 | Ukkestad et al. | 128/419 D |
| 3,888,260 | 6/1975 | Fischell | 128/419 PG |
| 3,920,024 | 11/1975 | Bowers | 128/419 PG |
| 3,924,641 | 12/1975 | Weiss | 128/419 PG |
| 3,939,844 | 2/1976 | Pequignot | 128/419 PG |
| 3,942,534 | 3/1976 | Allen et al. | 128/419 PG |
| 3,942,536 | 3/1976 | Mirowski et al. | 128/419 D |
| 3,945,387 | 3/1976 | Adams | 128/419 PG |
| 4,030,509 | 6/1977 | Heilman et al. | 128/419 D |
| 4,055,189 | 10/1977 | Auerbach et al. | 128/419 PG |
| 4,066,086 | 1/1978 | Alferness et al. | 128/421 |
| 4,088,138 | 5/1978 | Diack et al. | 128/419 D |
| 4,097,113 | 6/1978 | McKelvy | 339/256 R |
| 4,114,628 | 9/1978 | Rizk | 128/419 PG |
| 4,126,139 | 11/1978 | Walters et al. | 128/419 PG |
| 4,140,132 | 2/1979 | Dahl | 128/419 PG |
| 4,142,533 | 3/1979 | Brownlee et al. | 128/419 PT |
| 4,146,029 | 3/1979 | Ellinwood, Jr. | 128/260 |
| 4,163,451 | 8/1979 | Lesnick et al. | 128/419 PG |
| 4,164,944 | 8/1979 | Alley, III et al. | 128/419 PG |
| 4,165,749 | 8/1979 | Cansell | 128/419 D |
| 4,169,480 | 10/1979 | Digby et al. | 128/419 PG |
| 4,181,133 | 1/1980 | Kolenik et al. | 128/419 PG |
| 4,184,493 | 1/1980 | Langer et al. | 128/419 D |
| 4,201,219 | 5/1980 | Bozal Gonzalez | 128/419 PG |
| 4,202,340 | 5/1980 | Langer et al. | 128/419 D |
| 4,210,149 | 7/1980 | Heilman et al. | 128/419 D |
| 4,222,385 | 9/1980 | Backhouse | 128/419 PG |
| 4,223,678 | 9/1980 | Langer et al. | 128/419 D |
| 4,228,803 | 10/1980 | Rickards | 128/419 PG |
| 4,236,522 | 12/1980 | McDonald et al. | 128/419 PG |
| 4,280,502 | 7/1981 | Baker, Jr. et al. | 128/419 PG |
| 4,291,699 | 9/1981 | Geddes et al. | 178/419 D |
| 4,295,474 | 10/1981 | Fischell | 128/697 |
| 4,300,567 | 11/1981 | Kolenik et al. | 128/419 D |
| 4,312,356 | 1/1982 | Sowton et al. | 128/419 PG |
| 4,375,817 | 3/1983 | Engle et al. | 128/419 D |
| 4,384,585 | 5/1983 | Zipes | 128/419 D |
| 4,388,927 | 6/1983 | Schober | 128/419 PG |
| 4,403,614 | 9/1983 | Engle et al. | 128/419 D |
| 4,421,114 | 12/1983 | Berkovits et al. | 128/419 PG |
| 4,440,172 | 4/1984 | Langer | 128/419 D |
| 4,475,551 | 10/1984 | Langer et al. | 128/419 D |
| 4,485,818 | 12/1984 | Leckrone et al. | 128/419 PG |
| 4,576,170 | 3/1986 | Bradley et al. | 128/419 D |
| 4,958,632 | 9/1990 | Duggan | 128/419 PG |

OTHER PUBLICATIONS

M. Mirowski et al., "The Automatic Implantable Defibrillator: Toward the Development of the First Clinical Model," Proceedings of a Symposium on Management of Ventricular Tachycardia–Role of Mexiletine Held in Copenhagen, Denmark (May 25–27, 1978) pp. 655–664.

M. Mirowski et al., "The Automatic Implantable Defibrillator: A New Avenue," Medical and Surgical Management of Tachyarrhythmias, (ed. W. Bircks et al.) (1980) pp. 71–80.

J. Bourland et al., "An Animal Model For Testing Automatic Defibrillators," Medical Instrumentation, vol. 14, No. 1, (Jan.–Feb. 1980) pp. 15–17.

C. Wiggers, Physiology in Health and Disease, 5th Ed., Lea & Febiger, (1949) pp. 570–572.

W. Mandel et al., "Recurrent Reciprocating Tachycardias in the Wolff–Parkinson–White Syndrome: Control by the Use of a Scanning Pacemaker," Chest, vol. 69, No. 6, (Jun. 6, 1976) pp. 769–774.

M. Mirowski et al., "Standby Automatic Defibrillator: An Approach to Prevention of Sudden Coronary Death," Archives of Internal Medicine, vol. 126, No. 1, (Jul. 1970) pp. 158–161.

M. Mirowski et al., "The Development of the Transvenous Automatic Defibrillator," Archives of Internal Medicine, vol. 129, No. 5, (May 1972) pp. 773–779.

M. Mirowski et al., "Transvenous Automatic Defibrillator: Preliminary Clinical Tests of Its Defibrillating Subsystem," Transactions on American Society for Artificial Internal Organs, vol. 18, (Apr. 17–18, 1972) pp. 520–525.

M. Mirowski et al., "Ventricular Defibrillation through a Single Intravascular Catheter Electrode System," Abstract, Clinical Research, (Apr. 1971) p. 328.

M. Mower et al., "Ventricular Defibrillation with a Single Intravascular Catheter System Having Distal Electrode in Left Pulmonary Artery and Proximal Electrode in Right Ventricle or Right Atrium," Abstract, Clinical Research, (Apr. 1972) p. 389.

M. Mower et al., "Assessment of Various Models of Acetylcholine Induced Atrial Fibrillation for Study of Intra–Atrial Cardioversion," Abstract, Clinical Research, (Apr. 1972) p. 388.

J. Robinson et al., "Ventricular Tachycardia and Fibrillation with Implanted Electrical Pacemakers," British Heart Journal, vol. 27, No. 6, (1965) pp. 937–941.

R. Ruffy et al., "Influence of Acute Coronary Artery Occlusion on Direct Ventricular Defibrillation in Dogs," Medical Instrumentation, vol. 14, No. 1, (Jan.–Feb. 1980) pp. 23–26.

J. Schuder et al., "Ventricular Defibrillation in the Dog with a Bielectrode Intravascular Catheter," Archives of Internal Medicine, vol. 132, No. 1, (Jul. 1973) pp. 286–290.

P. Troup, "Implantable Cardioverters and Defibrillators," Current Problems in Cardiology, vol. 14, No. 12, (Dec. 1989) pp. 675–815.

A. Castellanos et al., "Implantable Pacemakers for Cardiac Tachyarrhythmias", Cardiac Arrhythmias: Mechanisms and Management, (1980) pp. 159–173.

J. Crick et al., "Variation in Tachycardia Termination Window with Posture and Exercise," Abstract, Procedings of the Second European Symposium on Cardiac Pacing, Florence, Italy, May 4–6, 1981, PACE: Pacing and Clinical Electrophysiology, vol. 4, (May–Jun. 1981) p. A–7.

P. Curry et al., "Dual–Demand Pacing for Refractory Atrioventricular Re–Entry Tachycardia," PACE: Pacing and Clinical Electrophysiology, vol. 2, No. 2, (Mar. 1979) pp. 137–151.

G. Ewy et al., "Electrode System for Permanent Implantable Defibrillators: Transvenous Catheter and Subcutaneous Plate Electrodes," Medical Instrumentation, vol. 12, No. 5, (Sep.–Oct. 1978) pp. 296–300.

S. Furman, "Appraisal and Reappraisal of Cardiac Therapy: Therapeutic Uses of Atrial Pacing," American Heart Journal, vol. 86, No. 6, (Dec. 1973) pp. 835–840.

J. Haft, "Treatment of Arrhythmias by Intracardiac Electrical Stimulation," Progress in Cardiovascular Diseases, (ed. E. Sonnenblick et al.) vol. 16, No. 6, (May–Jun. 1974) pp. 539–568.

D. Krikler et al., "Dual–Demand Pacing for Reciprocating Atrioventricular Tachycardia," British Medical Journal, (May 8, 1976) pp. 1114–1116.

H. Lew et al., "Control of Recurrent Ventricular Fibrillation by Transvenous Pacing in the Absence of Heart Block," American Heart Journal, vol. 73, No. 6, (Jun. 1967) pp. 794–797.

A. Nathan et al., "Clinical Evaluation of an Adaptive Tachycardia Intervention Pacemaker with Automatic Cycle Length Adjustment," PACE: Pacing and Clinical Electrophysiology, vol. 5, No. 2, (Mar.–Apr. 1982) pp. 201–207.

J. Schuder, "The Role of an Engineering Oriented Medical Research Group in Developing Improved Methods and Devices for Achieving Ventricular Defibrillation: The University of Missouri Experience," PACE: Pacing and Clinical Electrophysiology, vol. 16, No. 1, (Jan. 1993) pp. 95–124.

E. Sowton et al., "Use of a Multi–programmable Pacemaker in the Dual Demand Mode: Influence of Pacing Rate on Termination of Tachycardias," European Heart Journal, vol. 1, No. 3, (Jun. 1980) pp. 165–170.

D. Ward et al., "The Response of Regular Re–Entrant Supraventricular Tachycardia to Right Heart Stimulation," PACE: Pacing and Clinical Electrophysiology, vol. 2, No. 6, (Nov. 1979) pp. 586–595.

D. Zipes et al., "Artificial Atrial and Ventricular Pacing in the Treatment of Arrhythmias," Annals of Internal Medicine, vol. 70, No. 5, (May 1969) pp. 885–896.

W. Chardack et al., "Non–Invasive, Magnetically Coupled Control of Pulse Width of Implantable Pacemakers: Its Value in Reduction of Current Drain and Facilitatin of Patient Follow–Up," Cardiac Pacing: Proceedings of the IVth International Symposium on Cardiac Pacing, Groningen, The Netherlands, (Apr. 17–19, 1973) pp. 128–132.

L. Rubin, et al., "The Combined Standby Transvenous Defibrillator and Demand Pacemaker," Abstract, Circulation, vol. 46, No. 4, (Oct. 1972) pp. II–107.

J. Jenkins et al., "Computer Diagnosis of Supraventricular and Ventricular Arrhythmias: A New Esophageal Technique," Circulation, vol. 60, No. 5, (Nov. 1979) pp. 977–985.

L. Rubin et al., "Automatic Defibrillation and Pacing with a Tranvenous Electrode," Proceedings of the Fourth New England Bioengineering Conference, (May 7–8, 1976) pp. 427–430.

S. Epstein et al., "Experimental Acute Myocardial Infarction: Characterization and Treatment of the Malignant Premature Ventricular Contraction," Circulation, vol. 47, No. 3, (Mar. 1973) pp. 446–454.

J. Spann, Jr. et al., "Arrhythmias in Acute Myocardial Infarction: A Study Utilization an Electrocardiographic Monitor for Automatic Detection and Recording of Arrhythmias," The New England Journal of Medicine, vol. 271, No. 9, (Aug. 27, 1964) pp. 427–431.

R. Iyengar et al., "Continuous Monitoring of Ambulatory Patients with Coronary Disease," Progress in Cardiovascular Diseases, vol. 13, No. 4, (Jan. 1971) pp. 392–404.

J. Fisher et al., "Appraisal and Reappraisal of Cardiac Therapy: Cardiac Pacing and Pacemakers II, Serial Electrophysiologic–Pharmacologic Testing for Control of Recurrent Tachyarrhythmias," vol. 93, No. 5, (May 1977) pp. 658–668.

J. Jenkins et al., "Extension of a Single–Beat Algorithm Into Classification of Arrhythmias in Context," Computers in Cardiology, (Sep. 29–Oct. 1, 1977) pp. 305–309.

L. Watkins, Jr., et al., "Implantation of the Automatic Defibrillator: The Subxiphoid Approach," The Annals of Thoracic Surgery, vol. 34, No. 5, Seventh Annual Meeting of Society of Thoracic Surgeons, (Jan. 17–19, 1983) pp. 515–520.

M. Heilman et al., "Analysis of Four Implantable Electrode Systems for Automatic Defibrillator," Abstract, Supplement II to Circulation: An Official Journal of the American Heart Association, vol. 51–52, (Oct. 1975) p. II–194.

A. Langer et al., "A Novel Ventricular Fibrillation Detector for Implantable Defibrillator," Abstract, Supplements to Circulation: An Official Journal of the American Heart Association, vol. 51–52, (Jan.–Dec. 1975) pp. II–1, II–205.

A. Langer et al., "Considerations in the Development of the Automatic Implantable Defibrillator," Medical Instrumentation, vol. 10, No. 3, (May–Jun. 1976) pp. 163–167.

B. Lown et al., "Implanted Standby Defibrillators," Circulation: An Official Journal of the American Heart Association, vol. 46, (Oct. 1972) pp. 637–639.

B. Lown et al., "Approaches to Sudden Death from Coronary Heart Disease," Circulation: An Official Journal of the American Heart Association, vol. 44, (Jul. 1971) pp. 130–142.

B. McCallister et al., "Paroxysmal Ventricular Tachycardia and Fibrillation Without Complete Heart Block: Report of a Case Treated with a Permanent Internal Cardiac Pacemaker," The American Journal of Cardiology, vol. 18, (Jul.–Dec. 1966) pp. 898–903.

M. Mirowski et al., "The Automatic Implanting Defibrillator: Some Historical Notes," Cardiac Arrhythmias: Where to Go From Here? (ed. W. Brugada et al.), (1987) pp. 655–662.

M. Mirowski et al., "Feasibility and Effectiveness of Low–Energy Catheter Defibrillation in Man," Circulation: An Official Journal of the American Heart Association, vol. 47, (Jan.–Jun. 1973) p. 79–85.

M. Mirowski et al., "Implanted Defbrillators," Cardiac Defibrillation Conference, (Oct. 1–3, 1975) pp. 93–96.

A. Moss et al., "Termination and Inhibition of Recurrent Tachycardias by Implanted Pervenous Pacemakers," Circulation: An Official Journal of the American Heart Association, vol. 50 (Jul.–Dec. 1974) pp. 942–947.

J. Schuder et al., "Ventricular Defibrillation in the Dog Using Implanted and Partially Implanted Electrodes Systems," The American Journal of Cardiology, vol. 33, (Feb. 1974) pp. 243–247.

J. Schuder et al., "Ventricular Defibrillation with Catheter Having Distal Electrode in Right Ventricle and Proximal Electrode in Superior Vena Cava," Abstract, Supplement No. 2 of Circulation: An Official Journal of the American Heart Association, vols. 43 and 44, (Oct. 1971) p. II–99.

R. Spurrell et al., "An Implanted Atrial Synchronous Pacemaker with a Short Atrioventricular Delay for the Prevention of Paroxysmal Supraventricular Tachycardias," Journal of Electrocardiology, vol. 9, No. 1, (1976) pp. 89–96.

W. Tacker et al., "Electrical Defibrillation," CRC Press, Chapter 10, (1980) pp. 167–178.

D. Zipes et al., "Early Experience with an Implantable Cardioverter," The New England Journal of Medicine, vol. 311, No. 8, (Aug. 23, 1984) pp. 485–490.

T. Cheng, "The Transvenous Ventricular Pacing in the Treatment of Paroxysmal Atrial Tachyarrhythmias Alternating With Sinus Bradycardia and Standstill," The American Journal of Cardiology, vol. 22, (Jul.–Dec. 1968) pp. 874–879.

J. Crick et al., "Variation in Tachycardia Termination Window With Posture and Exercise," Abstract, Second European Symposium on Cardiac Pacing (May 4–6, 1981), p. 47.

J. Griffin et al., "Clinical Use of an Implantable Automatic Tachycardia–Terminating Pacemaker," American Heart Journal, Part 2, (Dec. 1980) pp. 1093–1096.

D. Heiman et al., "Suppression of Ventricular Arrhythmias by Transvenous Intracardiac Pacing," Journal of the American Medical Association, vol. 195, No. 13, (Mar. 28, 1966) pp. 172–175.

J. Hopps et al., "Electrical Treatment of Cardiac Arrest: A Cardia Stimulator–Defibrillator," Surgery, vol. 36, (Oct. 1954) pp. 833–849.

L. Kappenberger et al., "Programmed Stimulation for Long–Term Treatment and Non–Invasive Investigation of Recurrent Tachycardia," The Lancet, (Apr. 25, 1981) pp. 909–914.

M. Mirowski et al., "Termination of Malignant Ventricular Arrhythmias with an Implanted Automatic Defibrillator in Human Beings," The New England Journal of Medicine, vol. 303, No. 6, (Aug. 7, 1980) pp. 322–324.

G. Ryan et al., "Parodoxical Use of a Demand Pacemaker in Treatment of Supraventricular Tachycardia Due to the Wolff–Parkinson–White Syndrome," Circulation: An Official Journal of the American Heart Association, vol. 38, (Jul.–Dec. 1968) pp. 1037–1043.

E. Sowton et al., "Two Years' Clinical Experience with a Self–Searching Tachycardia Pacemaker" Abstract, The American Journal of Cardiology, vol. 47, (Jan.–Jun. 1981) p. 476.

G. Smith, "Iliofemoral Venous Thrombectomy: Indications, Technique, and Results in Forty–Five Cases," Circulation: An Official Journal of the American Heart Association, vol. 37, (Jan.–Jun. 1968) pp. 847–853.

H. Wellens et al., "Electrical Management of Arrhythmias With Emphasis on The Tachycardias," The American Journal of Cardiology, vol. 41, (May 22, 1978) pp. 1025–1034.

F. Zacouto et al., "On an Electronic Device Whereby the Cardiac Syncope Mechanism in Mammals Can Be Determined and a Corresponding Resuscitation Can Be Implemented," Societe De Biologie, vol. 155, No. 6, (Jun. 24, 1961) pp. 1257–1260, English Translation Attached.

"Line–Operated Synchronized Defibrillators," Health Devices, vol. 2, No. 5, (Mar. 1973) pp. 117–129.

R. Spurrel, "Artificial Cadiac Pacemakers," Cardiac Arrhythmias: The Modern Electrophysiological Approach (ed. D. Krikler et al.) (1975) pp. 238–258.

F. Zacouto et al., "Fundamentals of Orthorhythmic Pacing," Cardiac Pacing: Diagnostic and Therapeutic Tools, (ed. B. Luderitz) (1976) pp. 214–218.

H. Funke, "18 Months of Clinical Experience with the Implantable Optimized Sequential Stimulator (OSS)," Proceedings of the VIth World Symposium on Cardiac Pacing, Montreal (Oct. 2–5, 1979).

N. Smyth et al., "Permanent Pervenous Atrial AV Synchronous and AV Sequential Pacing," Cardiac Pacing: Proceedings of the IVth International Symposium on Cardiac Pacing, Groningen, The Netherlands, (Apr. 17–19, 1973) pp. 143–149.

C. Beck et al., "Ventricular Fibrillation of Long Duration Abolished by Electric Shock," Journal of the American Medical Association, vol. 135, No. 15, (Dec. 13, 147) pp. 957, 985–896.

L. Geddes et al., "The First Human Heart Defibrillation," The American Journal of Cardiology, vol. 52, No. 3, (Aug. 1983) pp. 403–405.

J. Gullett et al., "Optimum Duration of 60–Hz Current for Direct Ventricular Defibrillation in the Dog," Cardiovascular Research Center Bulletin, vol. 6, No. 3, (Jan.–Mar. 1968) pp. 117–123.

N. Gurvich et al., "Restoration of Heart Rhythm During Fibrillation by a Condenser Discharge," Americam Review of Soviet Medicine, vol. 4, No. 2, (Dec. 1946) pp. 252–256.

B. Lown et al., "Comparison of Alternating Current with Direct Current Electroshock Across the Closed Chest," The American Journal of Cardiology, vol. 10, No. 2, (Aug. 1962) pp. 223–233.

J. Jude et al., "An Experimental and Clinical Study of a Portable External Cardiac Defibrillator," Surgical Forum: Proceedings of the Forum Sessions Forty–Eighth Clinical Congress of the American College of Surgeons, Atlantic City, New Jersey, (Oct. 1962) pp. 185–187.

M. Mirowski et al., "Clinical Treatment of Life–Threatening Ventricular Tachyarrhythmias with the Automatic Implantable Defibrillator," American Heart Journal, vol. 102, No. 2, (Aug. 1981) pp. 265–270.

L. Watkins et al., "Automatic Defibrillation in Man: The Initial Surgical Experience," The Journal of Thoracic and Cardiovascular Surgery, vol. 82, No. 4, (Oct. 1981) pp. 492–500.

J. Hopps et al., "Electrical Teatment of Cardiac Arrest: A Cardiac Stimulator–Defibrillator," Surgery, vol. 36, (Jul.–Dec. 1954) pp. 833–849.

J. Gold et al., "Contour Graph for Relating Per Cent Success in Achieving Ventricular Defibrillation to Duration, Current, and Energy Content of Shock," American Heart Journal, vol. 98, No. 2, (Aug. 1979) pp. 207–212.

J. Jones et al., "Response of Cultured Myocardial Cells to Countershock–Type Electric Field Stimulation," The American Journal of Physiology, vol. 23, No. 2, (Aug. 1978) pp. H214–H222.

G. Jaros et al., "New Approaches to Fibrillation and Defibrillation of the Heart," S.A. Medical Journal, (Jan. 22, 1972) pp. 63–67.

R. Spurrell et al., "Implantable Automatic Scanning Pacemaker for Termination of Supraventricular Tachycardia," The American Journal of Cardiology, vol. 49, (Mar. 1982) pp. 753–759.

D. Ward et al., "Autodecremental Pacing—A Microprocessor Based Modality for the Termination of Paroxysmal Tachycardias," PACE: Pacing and Clinical Electrophysiology, vol. 3, (Mar.–Apr. 1980) pp. 178–191.

J. Fisher et al., "Termination of Ventricular Tachycardia with Bursts of Rapid Ventricular Pacing," The American Journal of Cardiology, vol. 41, (Jan. 1978) pp. 94–102.

C. Vassaux et al., "Cardioversion of Supraventricular Tachycardias," Circulation, vol. 39, (Jun. 1969) pp. 791–802.

A. Waldo et al., "Relevance of Electrograms and Transient Entrainment for Antitachycardia Devices," PACE: Pacing and Clinical Electrophysiology, vol. 7, No. 3, Part II, (May–Jun. 1984) pp. 588–600.

N. Gurvich et al., "Defibrillation of the Heart with Biphasic Electrical Impulses," Cardiology, Russian Journal, No. 7, (1967) pp. 108–112.

G. Ewy et al., "Electrode Catheter for Transvenous Defibrillation," Medical Instrumentation, vol. 10, No. 3, (May–Jun. 1976) pp. 155–158.

J. Schuder et al., "Transthoracic Ventricular Defibrillation with Square–Wave Stimuli: One Half Cycle, One Cycle, and Multicycle Waveforms," Circulation Research, vol. 15, No. 3, (Sep. 1964) pp. 258–264.

W. Tacker et al., "Defibrillation of the Dog Ventricles Using Single and Multiple Half–Sinusoidal Current Pulses," Cardiovascular Research Center Bulletin, vol. 10, No. 2, (Jul.–Sep. 1971) pp. 57–67.

L. Geddes et al., "Ventricular Defibrillation with Single and Twin Pulses of Half–Sinusoidal Current," Journal of Applied Physiology, vol. 34, No. 1, (Jan. 1973) pp. 8–11.

K. Black et al., "Transcutaneous Oxygen as an Indicator of Metabolic Adaptation in Ischemic Skin Flaps," Proceedings of the Association for the Advancement of Medical Instrumentation, 17th Annual Meeting, (May 9–12, 1982) pp. 15–16.

J. Schuder et al., "Asymmetrical Bidirectional Wave Defibrillation in Calves," 35th ACEMB, Philadelphia, PA, (Sep. 22–24, 1982) p. 41.

M. Niebauer et al., "Efficacy and Safety of the Reciprocal Pulse Defibrillator Current Waveform", Journal of the International Federation for Medical & Biological Engineering, vol. 22, No. 1, (Jan. 1984) pp. 28–31.

J. Schuder et al., "Transthoracic Ventricular Defibrillation in the 100 kg Calf with Symmetrical One–Cycle Bidirectional Rectangular Wave Stimuli," IEEE Transactions on Biomedical Engineering, vol. BME–30, No. 7, (Jul. 1983) pp. 415–422.

J. Schuder et al., "Defibrillation of 100 kg Calves with Asymmetrical, Bidirectional, Rectangular Pulses," Cardiovascular Research, vol. 18, No. 7, (Jul. 1984) pp. 419–426.

W. Tacker et al., "Minimum Duration of Capacitor Discharge Current for Indirect Ventricular Defibrillation in the Dog," Cardiovascular Research Center Bulletin, vol. 7, No. 1, (Jul.–Sep. 1968) p. 21–26.

L. Geddes et al., "Engineering and Physiological Considerations of Direct Capacitor–Discharge Ventricular Defibrillation," Journal of the International Federation for Medical and Biological Engineering, vol. 9, (1971) pp. 185–198.

J. Schuder et al., "Transthoracic Ventricular Defibrillation with Triangular and Trapezoidal Waveforms," Circulation Research, vol. 19, (Oct. 1966) pp. 689–694.

J. Jones et al., "Response of Cultured Myocardial Cells to Countershock–type Electric Field Stimulation," American Journal of Physiology, vol. 235, No. 2, (Aug. 1978) pp. H214–H222.

M. Mirowski, "Low–Energy Catheter Cardioversion of Atrial Tachyarrhythmias," Clinical Research, Abstract, vol. 22, No. 3, (Apr. 1974).

M. Mower et al., "Anatomical Consequences of Low–Energy Intra–Atrial Catheter Shocks," Clinical Research, Abstract, vol. 22, No. 5, (Mar. 1974) p. 291A.

M. Dwyer et al., "Regional Myocardial Blood Flow (MBF) in Transmural Myocardial Infraction," Abstract, Circulation, vol. 44, No. 4, (Oct. 1971) p. II–124.

M. Mirowski et al., "Transvenous Automatic Defibrillator as an Approach to Prevention of Sudden Death from Ventricular Fibrillation," Heart & Lung: The Journal of Critical Care, vol. 2, No. 6, (Nov.–Dec. 1973) pp. 867–869.

J. Morganroth et al., "The Athlete's Heart: Comparative Left Ventricular Dimensions of Collegiate Athletes Participating in Sports Requiring Isotonic or Isometric Exertion," Clinical Research, Abstract, vol. 22, No. 5, (Dec. 1974) p. 291A.

S. Levine et al., "Ventilatory Response to Tissue Hypoxia IV," Clinical Research, Abstract, vol. 22, No.3, (Apr. 1974) p. 508A.

M. Mower et al., "Patterns of Ventricular Activity During Catheter Defibrillation," Circulation, vol. 49, (May 1974) pp. 858–861.

M. Mirowski et al., "Low–Energy Catheter Cardioversion of Atrial Tachyarrhythmias," Clinical Research, Abstract, vol. 22, (1974) p. 290A.

M. Mirowski et al., "Prevention of Sudden Coronary Death Through Automatic Detection and Treatment of Ventricular Fibrillation (VF) Using a Single Intravascular Catheter (C) System," Circulation, vols. 42 and 44, (Oct. 1971) p. II–124.

J. Hartlaub, "Electronics in Cardiac Pacemakers," Proceedings of the Association for the Advancement of Medical Instrumentation, $14^{th}$ Annual Meeting, (May 20–24, 1979) p. 111.

L. Marion, "Programmables Excite Pacer Firms," Electronics, (Mar. 29, 1979) pp. 84–85.

C. Ragsdale, Harry Diamond Laboratories, Army Heart Monitor—Model IV, (Mar. 1970) pp. 1–132.

H. Wellens, Electrical Stimulation of the Heart in the Study and Treatment of Tachycardias, Chapter 7, University Park Press Baltimore, (1971).

E. Sowton, et al., "The Suppression of Arrhythmias by Artificial Pacemaking," The Lancet, Original Articles, London, (Nov. 21, 1964) pp. 1098–1100.

J. Schuder, "Standby Implanted Defibrillators," Archives of Internal Medicine, vol. 127, No. 2, (Feb. 1971) p. 317.

L. Rubin et al., "Automatic Defibrillation and Pacing with a Transvenous Electrode," Biotelemetry, Proceedings of the Fourth New England Bioengineering Conference, (1975) pp. 427–430.

I. Kruse et al., "Clinical Evaluation of a New Atrial Synchronous Ventricular Inhibited Pacemaker," VIth Symposium on Cardiac Pacing, Montreal (Oct. 2–5, 1979).

Intermedics, Inc., "Clinical Investigators Protocol For Intermedics Model 261–01 and Model 262–01, CyberTach™ 60, Multi–Parameter Programmable with Tachycardia Response Pulse Generator and Intermedics Model 525–01 CyberTech Programmer," (Aug. 1979) pp. 1–51.

R. Ripley, "An Overview of the Holter Procedure," Journal of Cardiovascular and Pulmonary Technology, (Aug./Sep. 1978), pp. 30–35.

Letter from M. Heilman to G. Rahmoeller at FDA (Jun. 22, 1976).

Intermedics, Inc., "General Distribution Notice, Subject: CyberTach™ 60," (Sep. 17, 1979).

J. Schuder et al., "Experimental Ventriuclar Defibrillation With An Automatic and Completely Implanted System," American Society for Artificial Internal Organs, vol. 16 (1970) pp. 207–212.

W. Holcomb et al., "A Demand Radio Frequency Cardiac Pacemaker," Medical & Biological Engineering, vol. 7, No. 5, (Sep. 1969) pp. 493–499.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–14 is confirmed.

New claim 15 is added and determined to be patentable.

*15. The cardioverting device of claim 1, wherein said third monitoring means includes a display.*

\* \* \* \* \*